(12) United States Patent
Pugia et al.

(10) Patent No.: US 8,462,332 B2
(45) Date of Patent: Jun. 11, 2013

(54) MULTI-LAYER SLIDES FOR ANALYSIS OF URINE SEDIMENTS

(75) Inventors: Michael J. Pugia, Granger, IN (US); Henry Lu, Westfield, IN (US)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 303 days.

(21) Appl. No.: 13/059,670

(22) PCT Filed: Aug. 18, 2009

(86) PCT No.: PCT/US2009/054108
§ 371 (c)(1),
(2), (4) Date: Feb. 18, 2011

(87) PCT Pub. No.: WO2010/022019
PCT Pub. Date: Feb. 25, 2010

(65) Prior Publication Data
US 2011/0149277 A1    Jun. 23, 2011

Related U.S. Application Data

(60) Provisional application No. 61/090,631, filed on Aug. 21, 2008.

(51) Int. Cl.
*G01N 21/01* (2006.01)
*G01N 1/10* (2006.01)

(52) U.S. Cl.
USPC .................................. 356/244; 356/246

(58) Field of Classification Search
USPC ................................ 356/244–246
See application file for complete search history.

(56) References Cited

U.S. PATENT DOCUMENTS

| | | | |
|---|---|---|---|
| 3,777,283 A | 12/1973 | Elkins | |
| 3,826,364 A | 7/1974 | Bonner et al. | |
| 4,308,028 A | 12/1981 | Elkins | |
| 4,441,793 A | 4/1984 | Elkins | |
| 4,761,381 A * | 8/1988 | Blatt et al. | 436/165 |
| 5,209,904 A * | 5/1993 | Forney et al. | 422/73 |
| 5,248,479 A * | 9/1993 | Parsons et al. | 422/412 |
| 5,699,794 A | 12/1997 | Fleck | |
| 5,700,559 A | 12/1997 | Sheu et al. | |

(Continued)

FOREIGN PATENT DOCUMENTS

| EP | 1069951 | 1/2001 |
|---|---|---|
| EP | 1070250 | 1/2001 |

(Continued)

OTHER PUBLICATIONS

International Search Report and Written Opinion of International Application No. PCT/US2009/054108 mailed on Oct. 6, 2009.

(Continued)

*Primary Examiner* — Gregory J. Toatley
*Assistant Examiner* — Jarreas C. Underwood
(74) *Attorney, Agent, or Firm* — Noam R. Pollack

(57) ABSTRACT

Visual analysis of urine samples is carried out with the use of a slide consisting of three layers containing an enclosed viewing chamber which receives a urine sample deposited by pipette into an opening on the outer layer of the slide. From the inlet opening the sample enters an inlet chamber in the middle layer and passes through a capillary passageway into the viewing chamber where it is inspected for particles and sediments.

17 Claims, 1 Drawing Sheet

U.S. PATENT DOCUMENTS

| | | | |
|---|---|---|---|
| 5,807,636 A | 9/1998 | Sheu et al. | |
| 5,837,377 A | 11/1998 | Sheu et al. | |
| 5,948,686 A | 9/1999 | Wardlaw | |
| 6,004,821 A * | 12/1999 | Levine et al. | 436/169 |
| 6,180,314 B1 | 1/2001 | Berndt | |
| 6,287,870 B1 | 9/2001 | Wardlaw | |
| 6,387,325 B1 | 5/2002 | Keusch et al. | |
| 6,387,708 B2 | 5/2002 | Wardlaw | |
| 6,448,088 B1 * | 9/2002 | Levine et al. | 436/164 |
| 6,521,463 B2 | 2/2003 | Wardlaw | |
| 6,544,793 B2 | 4/2003 | Berndt | |
| 6,555,387 B1 | 4/2003 | Berndt et al. | |
| 6,599,475 B1 | 7/2003 | Berndt et al. | |
| 6,599,480 B1 | 7/2003 | Scrivens et al. | |
| 6,723,290 B1 | 4/2004 | Wardlaw | |
| 6,819,408 B1 | 11/2004 | Scrivens et al. | |
| 6,825,926 B2 | 11/2004 | Turner et al. | |
| 6,867,049 B1 | 3/2005 | Scrivens et al. | |
| 6,953,550 B2 | 10/2005 | Sheppard, Jr. et al. | |
| 7,094,354 B2 | 8/2006 | Pugia et al. | |
| 2001/0033808 A1 | 10/2001 | Wardlaw | |
| 2001/0039056 A1 | 11/2001 | Wardlaw | |
| 2002/0119486 A1 * | 8/2002 | Oberhardt | 435/6 |
| 2006/0198765 A1 | 9/2006 | Gjerde et al. | |

FOREIGN PATENT DOCUMENTS

| | | |
|---|---|---|
| EP | 1070252 | 1/2001 |
| EP | 1079224 | 2/2001 |
| EP | 1188483 | 3/2002 |
| EP | 1190771 | 3/2002 |
| EP | 1566215 | 8/2005 |
| JP | 10185803 | 7/1998 |
| JP | 2000035384 | 2/2000 |
| JP | 2001108671 | 4/2001 |
| JP | 2001174456 | 6/2001 |
| JP | 2001255260 | 9/2001 |
| JP | 2002357772 | 12/2002 |
| JP | 2003227780 | 8/2003 |
| JP | 2006201367 | 8/2006 |
| JP | 2007010685 | 1/2007 |
| WO | 9944743 | 9/1999 |
| WO | 9945382 | 9/1999 |
| WO | 2005100539 | 10/2005 |
| WO | 2008050165 | 5/2008 |

OTHER PUBLICATIONS

European Search Report and Written Opinion of European Patent Application No. 09808687.9 issued on Mar. 27, 2012.

* cited by examiner

MULTI-LAYER SLIDES FOR ANALYSIS OF URINE SEDIMENTS

BACKGROUND OF THE INVENTION

This invention generally relates to analysis of urine for particles and sediments of various types. Examples include leukocytes, erythrocytes, epithelial cells, oval fat bodies, hyaline casts, granular casts, leukocytes casts, renal cell casts, waxy casts, fatty casts, uric acid crystals, calcium oxalate crystals, hippuric acid crystals, calcium phosphate crystals, triple phosphate crystals and the like. Such analyses are useful for determining whether a patient requires medical attention.

At present, urine sediment analysis may be done through manual microscopy, flow cytometry, flow cell imaging, and microfluidic slide imaging. Of these, microfluidic slide imaging has advantages over the others. Manual microscopy is accurate, but labor intensive and requires trained technicians. Flow cytometry and flow cell imaging are less accurate, although they require less manual labor. However, follow up with manual microscopy if often required. Examples of flow cell imaging and flow cytometry may be found in U.S. Pat. No. 6,825,926 and U.S. Pat. No. 3,826,364, respectively.

U.S. Pat. No. 5,699,794 discusses many other patents in the field and discloses an automated system and a cell used in urine sediment analysis. U.S. Pat. No. 3,777,283 discloses a plastic slide in which capillary force is used to draw a liquid specimen into a transparent viewing chamber. U.S. Pat. No. 4,441,793 discloses a slide for microscopic evaluation having one or two openings for introduction of a sample by a pipette into a viewing area. However, the slide does not separate the viewing chamber from the sample entry opening, which makes it more difficult to accurately read the images in a microscope. Another example of manual microscopy in a slide may be found in U.S. Pat. No. 6,004,821, where several types of analyses are carried out in a single sample-containing slide. In one analysis type, a portion of the urine sample is sent to a chamber for identifying urine casts. The chamber includes a water absorbent layer (e.g. a hydrogel) that removes the water from the sample, fixing the casts for visual inspection. In another type of analysis, bacteria and red and white blood cells are segregated and can be seen in a formed particle chamber having variable depth.

Analysis employing microfluidic techniques has become prominent in recent years for use with various biological samples, including urine and blood. In general, microfluidic disks or similar "chips" generally provide a group of interconnected chambers through which a fluid sample is passed to encounter various reagents. The reactions of the sample with the reagents provide information (e.g. color changes and the like) which can be related to the presence of analytes in the sample. In a typical microfluidic device, the chambers and interconnecting passageways are formed in a base layer, often a plastic material, and a cover is placed over the base. For an example, see U.S. Pat. No. 7,094,354. Such microfluidic devices can be adapted to visual analysis of urine samples for sediments. However, the cost of fabricating such microfluidic devices is rather high and less expensive designs would be desirable. The present inventors have found a less expensive, but still accurate method of analysis for urine sediments and other particles.

The '354 patent teaches the separation of particles in a microfluidic device, particularly the separation of red blood cells from a whole blood sample, with the use of low centrifugal force. Such separations were contrasted with the high centrifugal force used in bulk blood separation. An elongated chamber was used to allow accumulation of red blood cells at the bottom, while the separated plasma was withdrawn from the top of the chamber. The chamber's wall surfaces were made to have a surface energy matching or slightly lower than that of the red blood cells. The combination of the appropriate wall surface energy and capillary forces made possible the separation of red blood cells without using high centrifugal force.

If particles are to be identified in urine samples and studied, they should be relatively stationary. One means of positioning particles is shown in the '821 patent mentioned above, that is, by absorbing water from the sample the particles are immobilized. The '821 patent also shows the use of an angled chamber that apparently sorts the particles by their sizes. In the present invention, the particles and sediments are separated and immobilized by providing a viewing chamber having the appropriate surface energy, as will be discussed in more detail below.

SUMMARY OF THE INVENTION

The invention provides a means for carrying out visual analysis of urine particles and sediments. In one aspect, the invention is a method of visually inspecting urine samples for such particles and sediments. A sample of urine is introduced into a slide containing an inlet opening which receives the sample from a pipette. The liquid flows into an enclosed inlet chamber and then into an enclosed viewing chamber via a capillary passageway. The solids are separated and immobilized at the walls of the viewing chamber by appropriate selection of the wall's surface energy relative to the sample. The sample then can be visually inspected in the viewing chamber by appropriate means, e.g. a microscope or an automated instrument.

In another aspect, the invention is a slide adapted for visual inspection of urine samples for particles, e.g. red blood cells, or sediments, such as urine casts and calcium oxalate crystals. The slide includes three layers, an optically clear base layer, a middle layer containing at least one inlet chamber and a viewing chamber, the two chambers being connected by a capillary passageway, and finally a top optically clear layer containing an inlet opening for introducing the urine sample and a vent opening for releasing air from the viewing chamber. The optically clear layers have a high surface energy relative to that of the sample such that the particles and sediments are separated and immobilized by virtue of surface energy alone for ease of inspection. In general, the optically clear layers are expected to be highly hydrophilic. Particles and sediments will adhere to the optically clear layers when the surface energy of a surface relative to the bulk liquid of the sample is greater than the surface energy of the particles and sediments relative to the surface minus the surface energy of the particles and sediments relative to the bulk liquid. Mathematical representations of this relationship are included below.

DESCRIPTION OF PREFERRED EMBODIMENTS

In general, the invention provides a means for carrying out urine analysis using a slide in which a urine sample is introduced by a pipette and then flows through a capillary passageway into a region in which the sample can be optically examined for the presence of particles and sediments, such as those mentioned above.

Figure 1:
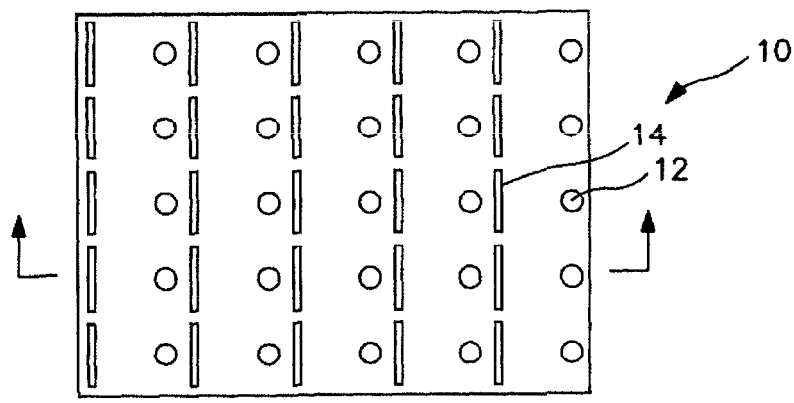
FIG. 1 is a plan view of the top layer of a slide of the invention.
Figure 2:
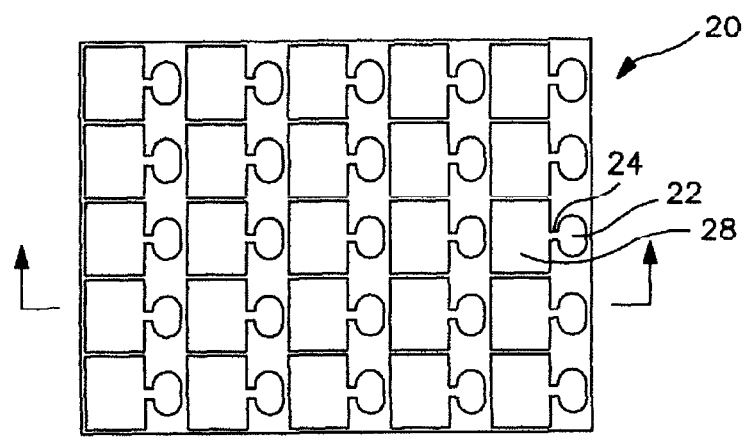
FIG. 2 is a plan view of the middle layer of a slide of the invention.
Figure 3:
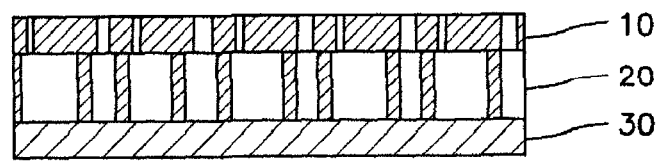
FIG. 3 is a sectional view of a three layer slide of the invention.

A preferred embodiment is shown in the FIGS. 1-3. The slide combines three layers (10, 20, and 30 in FIG. 3) and can receive 25 individual samples. The base layer 30 is an optically clear material, with high surface energy relative to the sample, such as cellulose acetate, the top layer 10 is a second sheet of the optically clear material with high surface energy relative to the sample (e.g. cellulose acetate) that has been cut to provide a vent slot 14 for removing air as liquid is introduced and an opening 12 through which the sample is introduced by a pipette. The middle layer 20 is a sheet of polyethylene terephthalate that has been cutout to provide an inlet chamber 22 and a viewing chamber 28, the two chambers connected by a capillary passageway 24. The middle layer has a sheet of an acrylic coated tape (e.g. 3M9494) on either side to bind the middle layer to both the top and bottom layer.

FIG. 1 shows the top layer 10 as it would be seen by one using the slide. The user would dispense urine from a pipette in a measured amount into inlet opening 12 and air would be displaced through vent 14. FIG. 2 shows the middle layer 20 and its cutouts that form two chambers and an interconnecting capillary passageway. The liquid would flow into inlet chamber 22 and then through capillary 24 into the viewing chamber 28 for inspection. The third layer 30 (see FIG. 3) is a base layer which, being optically clear, permits inspection from above or below the viewing chamber, that is, through the clear top layer or the clear base layer.

Although the illustrated slide contains 25 sets of cutouts forming sites for receiving and viewing 25 samples, it should be understood that the invention is not limited to any specific number of sets of test sites. They could number from one up to any convenient number depending on the capability of the equipment being used to view the samples.

In the slide shown in FIGS. 1-3, the length is 5 inches (127 mm) and the width 3.8 inches (96.5 mm) the thickness of the top and base layers is 0.005 inches (0.127 mm) while the middle layer including the pair of adhesive tapes, is 0.014 inches (0.356 mm) thick. Note that, since the three layers are quite thin, in FIG. 3 the thickness of each layer is much larger than the actual size. The sample size will be determined by the combined volume of the inlet chamber, the capillary, and the viewing chamber. The choice of sample size is not considered to be as important as that the volume of the viewing chamber is known, so that the amount of solids can be related to the volume of the actual sample. Typically, the sample size will be determined by the number of particles expected and may be from about 0.1 to 200 µL. In this example, the inlet port is generally circular with a diameter of about 2 mm, the air vent is a 1.5 by 15.8 mm slot, the volume of the inlet chamber is 1.53 µL, and the volume of the viewing chamber is about 90 µL. The viewing chamber has a width of 14.53 mm, a length of 17.78 mm, and a height of 0.35 mm. Other dimensions may be used if desired. For example, the viewing chamber might be elongated so that the sample is spread over a long and narrow area. This may achieve better separation of the particles and simplify the movement of the viewing means e.g. a camera for recording the appearance of the separated sediments. Thus, for a 90 µL sample, instead of the roughly square viewing area shown in the drawings, the viewing chamber might be about 80 mm long and 3.2 mm wide. In general, the depth of the viewing chamber particularly important since the sample will be inspected visually and spreading the sample minimizes the layering of particles and sediments which would limit visibility. In other embodiments the middle layer may have a thickness equal to or similar to that of the top layer and bottom layers so that the volume of the viewing chamber is about 45 µL rather than 90 µL. The separation of particles and segments at the surface of the top and bottom layer is facilitated by a shallow viewing chamber. In some embodiments, dyes will be added to assist in distinguishing between sediments of different types, e.g. between hyaline casts and waxy casts.

Also important are the dimensions of the capillary passageway used to transfer the urine sample from the inlet chamber to the viewing chamber. As explained in U.S. Pat. No. 7,094,354, the capillary must not have a dimension so small as to block particles from passing into the viewing chamber or from limiting liquid transfer. Thus, the smallest capillary dimension should be no less than about 100 µm. Preferably, the smallest dimension should be about 130 µm. Also, the length of the capillary should be limited so that separation of particles in the capillary is avoided. In the design shown in the figures, the capillary is a slot having a height equal to the thickness of the middle layer 20, i.e., 0.35 mm (350 µm) and a width of 200 µm. The side walls of the capillary are the polyethylene terephthalate of middle layer 20 and the top and bottom are the cellulose acetate of layers 10 and 30. Although the pipette applies some pressure when the urine sample is dispensed, the capillary should provide sufficient capillary force to transfer the urine sample rapidly. Consequently, the walls of the capillary will be hydrophilic in nature.

It has been found that the preferred cellulose acetate used for the top and base layers is unexpectedly effective in separating urine in the viewing chamber. In tests made with slides of the type illustrated in the figures the cellulose acetate used was a high performance OC-VLB grade film obtained from Grafix® Plastics, Cleveland, Ohio. As suggested previously, the red blood cells or other particles and sediments are attracted to the walls of the cellulose acetate viewing chamber, which is believed to have a suitable surface energy to separate and immobilize red blood cells and other particles and sediments for inspection. If other optically clear materials are chosen, their surface energy may require adjustment by techniques familiar to those in the art, such as adding suitable coatings.

The particles and sediments in urine were found to have similar surface energies adhering to a transparent viewing surface when the adhesion energy was matching or slightly lower than that of the urine and sediment. This may be expressed by the following equations:

$$\text{Free energy of adhesion} = \gamma \text{ sed-surface} - \gamma \text{ sed-liquid} - \gamma \text{ Surface-liquid}$$

Adhesion occurs when the free energy is at least zero or less. In the situation when:

$$Y \text{ surface-liquid} <= Y \text{ sed-surface} - Y \text{ sed-liquid}$$

wherein:

Y surface-liquid=the difference between the surface energy of the surfaces and the surface energy of the bulk liquid.

Y sed-surface=the difference between the surface energy of the sediments and other particles and the surface energy of the surfaces.

Y sed-liquid=the difference between the surface energy of the sediments and particles and the surface energy of the bulk liquid.

The difference between two phases is dependent on surface energy (erg/cm) of each phase whether surface and liquid, or surface and sediment or liquid and sediment. The surface energy of urine was measured as typically 55 to 58 erg/cm with a maximum range of 50 to 65 erg/cm. The surface energy of the urine sediment in said urine was discovered to be typically equal to urine, therefore adhesion is primarily dependent on the Y surface-liquid and favorable when the surface energy of the surface was greater or equal to urine.

Accordingly it was found that urine sediment comprised of cells, casts, crystals and other particles, are strongly adhered to the viewing surfaces when the surface energy (erg/cm) is greater than 50 dynes/cm. as indicated in the following comparative table:

| Surface | Surface energy (dynes/cm) | Contact Angle (Degrees) | Adhesion | Useful for high magnification viewing? |
|---|---|---|---|---|
| Coated Cellulose acetate | High (73) [1] | 7 (hydrophilic) | Strong | Yes |
| Cellulose acetate | Moderate (50 dynes/cm) [1] | 18 (hydrophilic) | Moderate | Yes |
| Polystyrene | Low (<33 dynes/cm) [1] | 86 (hydrophobic) | Weak | No |

[1] Surface energy determined from liquid contact angles measured by a goniometer using water as reference.

When viewing sediments and other particles at high magnification (e.g. >=100x) they are affected by Brownian motion and only when strongly adhered can they be properly inspected. The resolution of the microscope should be at least 1 μm and preferably capable of distinguishing between particles of 0.1 μm size. As the surface energy of the optical layers increases and the space between the optical layers decrease, the sediment becomes static upon adhesion. Surprisingly, as the surface energy of the layers increased, cells were less likely distort their natural shape upon adhesion. Red Blood Cells were particularly less likely to change cellular shape, to a crenated shape, under strong adhesion conditions. It is preferred that sediment be in as natural shape as possible to allow correct categorization.

The size of the viewing area depends on the viewing equipment used and also on the concentration and sizes of the particles and sediments to be inspected. Viewing equipment such as a microscope, typically uses a High Powered Fields (HPF) of to examine the sediment. A 400x magnification represents an area of ~330 microns by 330 microns size on the chamber. When the distance between the top and bottom optical layers is capillary gap of 100 microns, the volume of urine viewed is 0.011 uL. Clinical interpretation of urine sediment considered positive result to be a HRP typically containing between 3 to 5000 objects of sediment. Multiple HRP are measured as separate images to allow sufficient sampling. The number of HRP is typically 10 to 100 images are captured allowing 0.1 to 10 uL of the sampled volume to be measured. Multiple images can be measured by automated scanning stage that allows covering a number of HPF spaced in different location of the viewing area. The size and shape of the viewing must be at large enough to contain by the number of images to be measured. The images are arranged in pattern easy to be measured by the viewing equipment with minimum overlap and coverage errors.

The example represents a particularly useful sample size. The multiple images can be less than the sample size. It is noted that while the viewing chamber with a shallow depth shown is substantially square or rectangular, other dimensions and shapes are possible. Typically, the sample viewing chamber would be square, oval, round or rectangular and the images captured would be square, or rectangular images although or other shapes are not excluded.

The slides of the invention described above are suited for use in automated instruments adapted to accept and inspect such slides. Such instruments typically would be capable of positioning the slide and focusing the optics on each viewing chamber. Slides of the invention also may be inspected manually using microscopes having suitable magnification.

The materials used for optical layers can include hydrophilic glass and plastics. These material have been found to be very effective for bottom layers, being inexpensive, optically clear, flat and un-bending. Cell and urine sediment were found to adhere primarily to the bottom layer with any centrifugal force if allowed sufficient time to reach stasis. It is preferred that the time to stasis be as quick (<3 min) as possible to allow the analysis to be rapidly for system through-put. The time to adhere all urine sediment to the bottom layer (Time to statis) was reduced when the surface energy of the layers increased or the capillary gap between the layers decreased, as indicated in the following comparative table:

| Bottom materials | Contact Angle (mean, SD) | Surface Energy (dynes/cm) | Time to Stasis (min) | Capillary gap between layers(um) |
|---|---|---|---|---|
| Uncoated Polysytrene | 86 (2.1) | 33 | 10 | 330 |
| Mildly hydrophilic Glass Slide | 57.2 (1.5) | 50 | 5 | 330 |
| Mildly hydrophilic Glass Slide | 57.2 (1.5) | 50 | 3 | 100 |
| Cellulose acetate | 55.2 (1.2) | 50 | 3 | 100 |
| Coated Polystyrene | 31.8 (1.3) | 64 | 3 | 330 |
| Hydrophilic Glass Slide | 18.5 (1.8) | 69 | 3 | 330 |
| Coated Glass Slide | 7.3 (1.5) | 73 | 3 | 330 |
| Coated Glass Slide | 7.3 (1.5) | 73 | 0.5 | 100 |

*Cellulose acetate of used as top optical layer in all cases.

As the cells adhere to the bottom layer after stasis, the bottom layer can be made of thicker materials and not impact working distance of the microscope. is only limited by the top optical layer and the adhesive gap. A minimal working of ~0.9 mm is preferred for the typical microscopic lens for 400x magnification. Using unbending and flat bottom material is preferred as this layer becomes the focal plane that is used to capture the image of the sediment. A bottom layer with <1 um variation in the flatness of this layer is desired as not to require continuous focusing during image capture and allows the microscope to be calibrated easier between slides.

The materials for the bottom and top layer can be different as long as the top and bottom layers are optically clear materials of a combined effective surface energy of >=50 dyne/cm. Examples can include the combination of materials such as glass and plastics. The surface energy of these materials may have to be adjusted by known methods, such as plasma coating and polymer coating. Typical coating methods such as spray coating, spin coating, roller coating and the like maybe used.

The middle layer also could be made of any material of a defined thickness, such as cellulose acetate, plastics, adhesive or glass. This layer does not have to be optically clear but can be optically clear. The design in its simplest form is three layers such as a cellulose acetate top layer, a double-sided acrylic tape middle layer and glass bottom later. The thickness of the middle layer is considered to be more important than the material used. Rather than sealing the three layers with double sided tape, other techniques, such as radio frequency welding, could be used.

As will be evident, the urine inspection slide is less expensive to make than the typical microfluidic device. The precision manufacturing needed for microfluidic devices where a defined liquid sample contacts a defined amount of reagents is less important when urine particles and sediments are to be measured. Thus, it is not necessary to make a molded plastic base, polish it, treat it to adjust surface energy to affect liquid flow, and seal the base with a top cover. In contrast, the present three layer inspection slide of the invention is simple to make, provides a clear view of the sample, and yet contains the samples without leaking.

The invention claimed is:

1. A sample slide for visually inspecting samples comprising:
   (a) a base layer of optically clear material;
   (b) a middle layer containing at least one set of cutouts forming a test site, said cutouts forming at least one inlet chamber for receiving a sample, at least one viewing chamber, and at least one hydrophilic capillary passageway in fluid communication between said inlet chamber and said viewing chamber;
   (c) a top layer of optically clear material, said top layer containing cutouts forming openings for introducing said sample into said inlet chamber and for venting air from said viewing chamber;
   wherein said optically clear materials of (a) and (c) have a surface energy relative to the surface energy of said samples such that the particles and sediments are separated and immobilized on the surface of said optically clear materials.

2. A sample slide of claim 1 wherein said optically clear materials have a surface energy of at least 50 dynes/cm.

3. A sample slide of claim 2 wherein said optically clear materials of (a) and (c) are cellulose acetate.

4. A sample slide of claim 1 wherein said middle layer is made of polyethylene terephthalate.

5. A sample slide of claim 1 wherein said middle layer of (b) is bound and sealed to said top layer of (a) and said bottom layer of (c) by double-sided adhesive tape.

6. A sample slide of claim 1 containing 25 sets of cutouts forming a set of test sites.

7. A sample slide of claim 1 wherein said sample is about 2 to 200 µL.

8. A sample slide of claim 1 wherein said middle layer has a thickness of about 0.100 to 0.35 mm and said top has thickness of allowing a working distance of at least 0.9 mm.

9. A sample slide of claim 1 wherein said capillary passageway has no dimension smaller than 100 µm.

10. A sample slide of claim 1 wherein said viewing chamber has a volume of about 0.1 to 200 µL.

11. A method of visually inspecting samples comprising:
    (d) obtaining a sample;
    (e) introducing said sample of (a) into a sample slide; and
    (f) inspecting said sample of (a) within said sample slide;
    wherein said sample slide comprises a base layer of optically clear material having a high surface energy relative to the surface energy of said samples, a middle layer containing at least one set of cutouts forming a test site, said cutouts forming at least one inlet chamber for receiving said sample, at least one viewing chamber, and at least one hydrophilic capillary passageway in fluid communication between said inlet chamber and said viewing chamber; and a top layer of said optically clear material, said top layer containing cutouts forming openings for introducing said sample into said inlet chamber and for venting air from said viewing chamber.

12. The method of claim 11 wherein said optically clear material has a surface energy of about 38-50 dynes/cm.

13. The method of claim 11 wherein said optically clear material is cellulose acetate.

14. The method of claim 11 wherein said middle layer is made of polyethylene terephthalate.

15. The method of claim 11 wherein said middle layer bound and sealed to said top layer and said base layer by double-sided adhesive tape.

16. The method of claim 11 wherein said slide contains 25 sets of cutouts.

17. The method of claim 11 wherein said particles and sediments are immobilized at the surface of said optically clear top and bottom layers.

* * * * *